United States Patent [19]
Box et al.

[11] Patent Number: 5,154,691
[45] Date of Patent: Oct. 13, 1992

[54] POST SURGICAL PILLOW SLING

[76] Inventors: Robert A. Box; Olivia J. Box, both of 133 Mobile Ave., Trussville, Ala. 35173

[21] Appl. No.: 608,275

[22] Filed: Nov. 2, 1990

[51] Int. Cl.⁵ .......................... A61F 5/00; A61F 5/37
[52] U.S. Cl. ......................................... 602/5; 602/19; 128/875
[58] Field of Search .................. 121/875, 874, 78, 94, 121/106.1, 878, 888, 889; 5/431-444; 2/49 R, 2.5, 102, 44, 51; 602/4, 19

[56] References Cited

U.S. PATENT DOCUMENTS

| | | | |
|---|---|---|---|
| 1,621,323 | 3/1927 | Horn | 128/94 |
| 3,554,190 | 1/1971 | Kaplan | 2/44 |
| 4,079,464 | 3/1978 | Roggin | 2/2.5 |
| 4,413,357 | 11/1983 | Sacks | 2/2.5 |
| 4,497,069 | 2/1985 | Braunhut | 2/2.5 |
| 4,526,164 | 7/1985 | Bihl | 128/94 |
| 4,683,601 | 8/1987 | Lagin | 5/431 |
| 4,697,285 | 10/1987 | Sylvester | 2/2.5 |
| 4,829,613 | 5/1989 | Yon | 5/436 |
| 4,832,053 | 5/1989 | McCarthy | 128/874 |
| 4,847,913 | 7/1989 | Chen | 2/2.5 |
| 4,891,846 | 1/1990 | Sager | 2/102 |
| 4,960,112 | 10/1990 | Anderegg | 128/78 |

Primary Examiner—Michael A. Brown
Attorney, Agent, or Firm—Fleit, Jacobson, Cohn, Price, Holman & Stern

[57] ABSTRACT

A sling to hold and support a pillow or other stuffing material for use by patients during their recovery period from major surgical procedures such as cardiac, abdominal or pelvic surgical procedures. The sling supports the pillow or other stuffing material from the patient in a position to enable the patient to easily and quickly use the pillow or stuffing material as a "cough pillow". Supporting the "cough pillow" in close proximity to the area on which the surgical procedure is formed and in a position for ready access and grasping by the patient, enables the patient to have free use of their hands and upper extremities but yet maintains the pillow or stuffing material in position for immediate use. The sling includes a casing constructed of flexible, fabric-like material which may be rectangular in form or other desired shapes with one surface of the casing having an opening to enable insertion of a conventional hospital pillow which has been folded or other stuffing material such as "fiberfill" or other similar material. The casing is provided with an attachment strap or straps to secure the sling to a patient in close proximity to the area of a surgical procedure and in a position for ready access by the patient thus enabling the patient to use the sling and pillow or stuffing material as a "cough pillow" especially when a cough response occurs unexpectedly and spontaneously.

3 Claims, 1 Drawing Sheet

POST SURGICAL PILLOW SLING

BACKGROUND OF THE INVENTION

1. FIELD OF THE INVENTION

The present invention relates to a sling to hold and support a pillow or other stuffing material for use by patients during their recovery period from major surgical procedures such as cardiac, abdominal or pelvic surgical procedures. The sling supports the pillow or other stuffing material from the patient in a position to enable the patient to easily and quickly use the pillow or stuffing material as a "cough pillow". Supporting the "cough pillow" in close proximity to the area on which the surgical procedure is formed and in a position for ready access and grasping by the patient, enables the patient to have free use of their hands and upper extremities but yet maintains the pillow or stuffing material in position for immediate use. The sling includes a casing constructed of flexible, fabric-like material which may be rectangular in form or other desired shapes with one surface of the casing having an opening to enable insertion of a conventional hospital pillow which has been folded or other stuffing material such as "fiberfill" or other similar material. The casing is provided with an attachment strap or straps to secure the sling to a patient in close proximity to the area of a surgical procedure and in a position for ready access by the patient thus enabling the patient to use the sling and pillow or stuffing material as a "cough pillow" especially when a cough response occurs unexpectedly and spontaneously.

2. DESCRIPTION OF THE PRIOR ART

It is well known to utilize a "cough pillow" when a patient is recovering from surgical procedures or otherwise finds that it is necessary or desirable to prevent complications or when engaged in deep breathing or coughing exercises by holding the pillow against the surface area of the incision site. The following patents relate to this field of endeavor.

- U.S. Pat. No. 4,683,601
- U.S. Pat. No. 4,712,258
- U.S. Pat. No. 4,736,477
- U.S. Pat. No. 4,829,613

The patents listed above include various types of devices to be held against a patient. The Lagin device is constructed in a manner that a patient must put his arms into an appropriate place in relation to the pillow prior to coughing which requires that the patient keep up with his "cough pillow" by carrying it in his hands or locating it quickly when the need to cough occurs. The Yon patent discloses a heart-shaped pad to be held by the patient when coughing which again requires that the patient keep up with his "cough pillow" by either carrying it in the hands or finding it quickly when the need to cough occurs. The patents to Moore and Eves disclose pad devices but are not related to use of such devices as a "cough pillow".

None of the above patents disclose the particular structure of the present invention which supports a pillow or stuffing material from a patient to enable the patient to quickly and easily locate the pillow or stuffing material and position the pillow or stuffing material in the desired location even when the onset of coughing is unexpected and spontaneous and incapable of being suppressed for the length of time necessary to locate a pillow which may be spaced from and not immediately accessible to the patient.

SUMMARY OF THE INVENTION

An object of the present invention is to provide a sling for a pillow, stuffing material or similar pad-like material to support the same from a patient to enable the patient to immediately locate and gain control of the pillow, stuffing material or padlike material in order to place it against a surface area of the patient and enable the patient to exert a force to bias the pillow, stuffing material or pad-like material toward the surface area of the patient thereby forming a "cough pillow" during a post-surgical procedure or when performing deep breathing or coughing exercises to prevent complications such as pneumonia.

A further object of the invention is to provide a sling as set forth in the preceding object capable of being used by patients of all ages including neonatal patients that may have surgical procedures performed as well as children and adults including those that have had cardiac surgery, abdominal surgery or pelvic surgery with all patients benefiting from the "cough pillow" being supported from the patient in a manner to enable it to be readily available to the patient for use during an unexpected cough experience.

A further object of the invention is to provide a post-surgical pillow sling in accordance with the preceding objects which is relatively inexpensive to manufacture but is yet effective in supporting a pillow, stuffing material or pad-like material in readily accessible position in relation to a patient desiring to use the same as a "cough pillow".

These together with other objects and advantages which will become subsequently apparent reside in the details of construction and operation as more fully hereinafter described and claimed, reference being had to the accompanying drawings forming a part hereof, wherein like numerals refer to like parts throughout.

DESCRIPTION OF THE PREFERRED EMBODIMENTS

Figure 1:
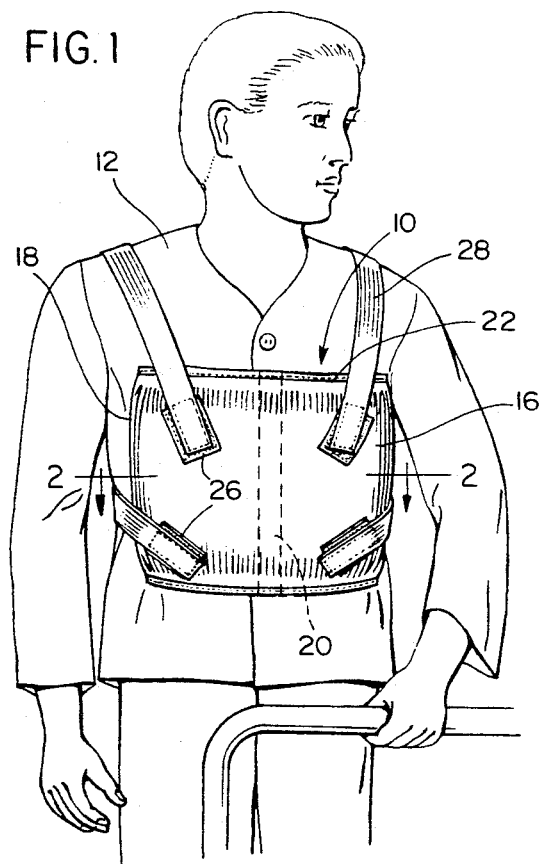
FIG. 1 is a front perspective view of the sling of the present invention illustrating the manner in which it is associated with a patient.
Figure 3:
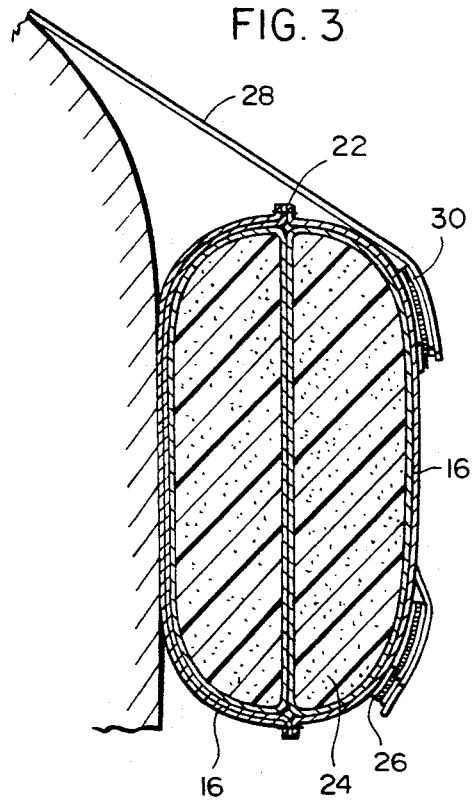
FIG. 3 is a transverse, sectional view taken substantially upon a plane passing along section line 3—3 on FIG. 2 illustrating further structural details of the sling.
Figure 2:
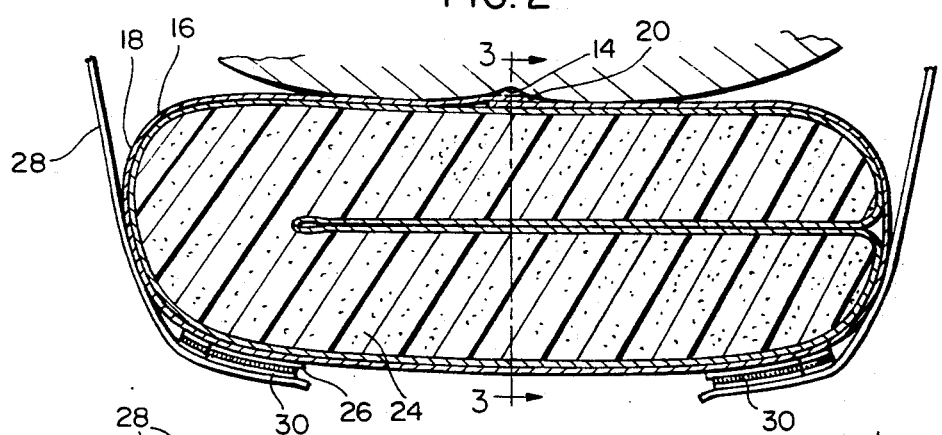
FIG. 2 is a longitudinal sectional view taken along section line 2—2 on FIG. 1 illustrating the structural details of the sling with a folded pillow positioned therein.
Figure 4:
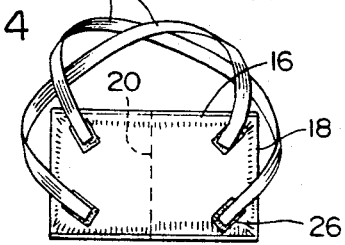
FIG. 4 is a fragmental elevational view, on an enlarged scale, illustrating the attachment of the supporting straps to the sling.

Referring now specifically to the drawings, the post-surgical sling for a pillow or other stuffing materials is generally designated by reference numeral 10 and is positioned in relation to a patient 12 to support it generally in overlying and aligned relation with a surgical site such as indicated by reference numeral 14 so that the sling 10 and the pillow or other stuffing material can be readily located and clutched to the surface of a surgical incision in order for it to serve as a type of body splint thereby greatly increasing the patient's comfort level especially when a sudden and unexpected coughing urge occurs.

The sling 10 is constructed of a sheet of fabric or fabric-like material 16 that is folded about transverse end areas 18 with the free ends thereof overlapping as at 20 adjacent a midpoint thereof. The bottom and top edges of the sheet of material 16 are stitched together along stitch lines 22 thus forming a casing having a smooth front and overlapping edges at the central portion of the rear of the sling. The sheet of material 16 may be of various sizes and constructed of washable material such as cotton, blends of cotton and polyester or other various materials which can be laundered in a conventional manner. Alternatively, the sheet of material may be constructed of a non-woven, inexpensive, disposable material having the same general shape and configuration as described and which may be glued to form the seams or the seams may be formed by heat sealing. The overall configuration of the sling 10 is rectangular and may be constructed of different sizes for use by adults, children or neonatal patients with the overlapping edges 20 providing an opening to enable insertion of a folded hospital pillow 24 therein with the bulkiness of the pillow serving to keep the opening defined by the overlapping ends 20 in closed position. While a folded regular bed pillow has been shown as positioned in the sling, various stuffing materials may be employed including polyester fiberfill or other flexible filler material which can be held against a surgical site 14 to enable the sling and the stuffing material therein to be utilized as "coughing pillow".

The front or outer surface of the sheet of material 16 includes corner patches 26 of the loop component of a hook and loop fastener material which is available commercially under the trademark "VELCRO". A fastening patch 26 is oriented at each corner of the front of the sling and is inclined to provide adjustment to a pair of supporting straps 28 which are relatively narrow and each of which includes a fastening patch 30 on the end thereof which is the hook component of the hook and loop fastener material to enable the straps to be adjusted to some extent in relation to the sling 16. As illustrated, the straps extend across the shoulders and around the chest cavity into a crossed relation at the rear of the patient 12 which supports the sling and pillow or stuffing 24 therein in position in front of the chest area of the patient 12. The straps may have the width of 2" and be of varying lengths and made of slightly resilient or stretchy material with the hook component on the fastener patch 30 enabling some degree of adjustment of the straps. The straps cross between the shoulder blades of the patient and, as illustrated in FIG. 1, hold the sling and stuffing material therein in position for immediate access and generally in overlying registry with the surgical site 14.

Figure 5:
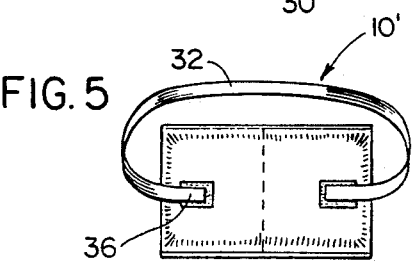
FIG. 5 is a elevational view illustrating another embodiment of the sling in which a single supporting strap is used.

FIG. 5 illustrated an embodiment of the invention in which the sling 10[1] is substantially the same except that instead of using two supporting straps, a single wide supporting strap 32 is utilized which may be 4" in width and each end of the sling 10[1] is provided with a patch of loop component of a hook and loop pile fastener as designated by numeral 34 and each end of the strap 32 is provided with a patch 36 of the hoop component of a hook and loop pile fastener assembly. This type of strap 32 can be used in encircling relation to the chest area or positioned at a lower position in relation to the torso for use with surgical procedures involving the abdominal or pelvic cavity. As indicated, the sling and supporting strap structure can be varied in size to enable effective use of the device by neonatal patients, children or youthful patients as well as adult patients and enables free use of the hands of the patient without the necessity of the patient hand carrying a "coughing pillow" or frantically searching for a "coughing pillow" in the event of a sudden and unexpected necessity to cough thereby enabling a patient to provide inward pressure on a surgical site to increase the comfort level of the patient and to decrease strain which may be placed on the surgical site when coughing or during other types of movement.

The device is especially useful to patients who have undergone cardiac, abdominal or pelvic surgical procedures or in other situations where it is desirable to provide a body splint to a portion of the human anatomy. Use of the sling aids in and facilitates coughing which is required for optimal respiratory function following such procedures. The sling itself does not apply any noticeable pressure that would impede normal chest expansion that is desired by coronary patients but when adjusted and used for the abdominal or pelvic patient, the sling can serve as a type of "body splint" to increase the comfort level of the patient. By using the sling, a patient is capable of freely moving and freely engaging in various activities including lying in bed, walking, eating, holding or carrying objects and otherwise conducting normal activities without the frustration of having to hand carry a pillow and search for the pillow when coughing is necessary or desired. The sling can also function as a device for holding the pillow against the incision site and the patient can then lie semi-prone or roll from side-to-side without repositioning the pillow. In addition, the sling can be used by non-surgical patients for positioning the pillow for anatomical support and the hook and loop pile fasteners allow for quick and easy removal of the sling as well as adjustment for conditioning the sling for use with individual patients.

When used with a neonatal patient, the straps may be 1" or less in width and, in some instances, permanently attached short straps can be used and in some instances, the hook component of the hook and loop fastener can be on the short straps and the loop component attached to the bedding or a pad beneath a neonatal patient to secure the sling in position. Also, the shape of the sling can be varied to simulate a known animal or object that may be attractive to a neonatal patient. When used by an adult patient, immediate access to a "coughing pillow" reduces the anxiety of the patient as well as frustration which may occur when the patient is frantically trying to locate a "coughing pillow" which has been placed in an area spaced from the location of the patient when coughing becomes necessary or is desired. Freedom of the hands also enables the patient to take an IV pole or oxygen supply with them when walking during their recovery period and also enables post-surgical deep breathing or coughing exercises which are encouraged to prevent complications such as pneumonia and when spontaneous coughing occurs. The sling also is significant when the patient leaves the hospital and continues recovery at home by enhancing their comfort during transportation and during the recovery process at home or at a nursing home. Also, the sling enables the device to be used as a positioning aid for patients by providing a sling and pillow or stuffing unit that can be used for anatomical support of the patient.

The foregoing is considered as illustrative only of the principles of the invention. Further, since numerous modifications and changes will readily occur to those skilled in the art, it is not desired to limit the invention to the exact construction and operation shown and described, and, accordingly, all suitable modifications and equivalents may be resorted to, falling within the scope of the invention.

What is claimed as new is as follows:

1. A coughing pillow assembly for post-surgical recovery by patients who have undergone cardia, abdominal or pelvic surgical procedures comprising a sling in the form of a casing a flexible fabric material including an outer panel and an inner panel, the inner panel having an accessopening extending substantially between opposite peripheral edge portions of the casing, said opening being defined only by overlapping edges of the flexible material forming the inner panel, said inner panel adapted to be positioned in overlying engaging relation to a surgical site thereby eliminating any discomfort that might be caused by rigid fastening devices forming a closure for the access opening, cushioning means in the form of stuffing material positioned interiorly of the casing and substantially filling the casing, resilient strap means connected with said casing and extending around a portion of the anatomy of a patient to resiliently retain the casing and cushioning means in overlying relation to a surgical site without requiring the use of the hands and arms of the patient to hold the casing in position, and means adjustably connecting the strap means to the casing to enable the casing to be supported on patients of various sizes, on various portions of the human anatomy and varying the resilient force imparted to the casing.

2. The assembly as defined in claim 1 wherein said means connecting the resilient strap means to the casing includes a plurality of loop components of a hook and loop pile fastener on the casing and a plurality of hook components of a hook and loop pile fastener on the strap means with at least one of the loop and hook components being elongated to enable adjustment of the points of attachment of the strap means to the casing.

3. The structure as defined in claim 2 wherein said strap means includes a pair of straps having the ends thereof adjustably connected to the casing and extending around a portion of the anatomy of the user with the straps being crossed in remote relation to the casing, said loop components being diagonally arranged on the casing whereby the long dimension of the loop components are generally parallel to the lengthwise dimension of the end portion of the straps, said stuffing material being in the form of a standard head pillow folded in half with the straps retaining the assembly in position on the patient in overlying relation to a surgical site without requiring the use of the hands of the patient thereby enabling the patient to be ambulatory and use their hands and arms for various purposes with the patient being assured that the coughing pillow assembly is always in position for use when coughing.

* * * * *